(12) United States Patent
Veasey et al.

(10) Patent No.: US 11,400,218 B2
(45) Date of Patent: Aug. 2, 2022

(54) HOUSING FOR AN INJECTION DEVICE AND INTERCONNECTION OF HOUSING COMPONENTS

(71) Applicant: SANOFI-AVENTIS DEUTSCHLAND GMBH, Frankfurt am Main (DE)

(72) Inventors: Robert Veasey, Warwickshire (GB); David Aubrey Plumptre, Worcestershire (GB); Matthew Jones, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 114 days.

(21) Appl. No.: 15/559,300

(22) PCT Filed: Mar. 21, 2016

(86) PCT No.: PCT/EP2016/056102
§ 371 (c)(1),
(2) Date: Sep. 18, 2017

(87) PCT Pub. No.: WO2016/150897
PCT Pub. Date: Sep. 29, 2016

(65) Prior Publication Data
US 2018/0064876 A1    Mar. 8, 2018

(30) Foreign Application Priority Data
Mar. 23, 2015 (EP) .................................... 15160252

(51) Int. Cl.
*A61M 5/24* (2006.01)
*A61M 5/34* (2006.01)
*A61M 5/315* (2006.01)

(52) U.S. Cl.
CPC .............. *A61M 5/24* (2013.01); *A61M 5/347* (2013.01); *A61M 5/31566* (2013.01); *A61M 2005/2407* (2013.01); *A61M 2005/2492* (2013.01)

(58) Field of Classification Search
CPC .... A61M 5/24; A61M 5/347; A61M 5/31566; A61M 2005/2407; A61M 2005/2403;
(Continued)

(56) References Cited

U.S. PATENT DOCUMENTS 533,575 A     2/1895   Wilkens
3,543,755 A * 12/1970  Kessel .................... A61M 5/24
                                                            604/415
(Continued)

FOREIGN PATENT DOCUMENTS

CA    2138528    2/1994
CA    2359375    7/2000
(Continued)

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.
(Continued)

*Primary Examiner* — Dung T Ulsh
(74) *Attorney, Agent, or Firm* — Fish & Richardson P.C.

(57) ABSTRACT

The present disclosure relates an elongated housing for an injection device for delivery of a liquid medicament, the housing comprising:
a tubular-shaped cartridge holder to accommodate a cartridge filled with the medicament and comprising a proximal connecting end,
a body to accommodate a drive mechanism operably engageable with a piston of the cartridge, wherein the
(Continued)

body comprises a distal connecting end connectable to the proximal connecting end, wherein one of the proximal connecting end and the distal connecting end comprises an insert section, wherein the other one of the proximal connecting end and the distal connecting end comprises a receptacle to axially receive the insert section, wherein the insert section comprises at least one fastening element to positively engage with a complementary-shaped fastening element of the receptacle to provide an axial interlock of the cartridge holder and the body, wherein the fastening elements of the insert section and the receptacle comprise at least one pair of a radial protrusion mating with a radial recess provided on an inside wall of the receptacle and on an outside wall of the insert section and wherein a radial depth of the radial recess is smaller than a thickness of the sidewall of the insert section or a thickness of a sidewall of the receptacle.

23 Claims, 4 Drawing Sheets

(58) Field of Classification Search
CPC .. A61M 2005/2492; A61M 2005/2485; A61M 2005/2488; A61M 2005/2496
See application file for complete search history.

(56) References Cited

U.S. PATENT DOCUMENTS

| | | | |
|---|---|---|---|
| 4,865,591 A | 9/1989 | Sams | |
| 5,092,842 A | 3/1992 | Bechtold | |
| 5,226,895 A | 7/1993 | Harris et al. | |
| 5,226,896 A | 7/1993 | Harris | |
| 5,279,586 A * | 1/1994 | Balkwill | A61M 5/3158 222/309 |
| 5,304,152 A | 4/1994 | Sams | |
| 5,320,609 A | 6/1994 | Haber et al. | |
| 5,378,233 A | 1/1995 | Haber | |
| 5,383,865 A | 1/1995 | Michel | |
| 5,391,157 A | 2/1995 | Harris | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,807,346 A | 9/1998 | Frezza | |
| 5,820,602 A | 10/1998 | Kovelman | |
| 5,851,079 A | 12/1998 | Horstman | |
| 5,921,966 A | 7/1999 | Bendek et al. | |
| 5,957,896 A | 9/1999 | Bendek | |
| 5,961,495 A | 10/1999 | Walters et al. | |
| 6,004,297 A * | 12/1999 | Steenfeldt-Jensen | A61M 5/31585 604/207 |
| 6,048,336 A * | 4/2000 | Gabriel | A61M 5/315 604/211 |
| 6,146,361 A * | 11/2000 | DiBiasi | A61M 5/347 604/232 |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 * | 6/2001 | Giambattista | A61M 5/31551 604/207 |
| 6,562,006 B1 | 5/2003 | Hjertman | |
| 6,613,023 B2 | 9/2003 | Kirchhofer | |
| 6,699,224 B2 | 3/2004 | Kirchhofer | |
| 6,932,794 B2 | 8/2005 | Giambattista | |
| 6,936,032 B1 | 8/2005 | Bush, Jr. et al. | |
| 7,169,132 B2 | 1/2007 | Bendek | |
| 7,241,278 B2 | 7/2007 | Moller | |
| 7,678,084 B2 | 3/2010 | Judson | |
| 8,187,233 B2 | 5/2012 | Harms et al. | |
| 2002/0052578 A1 | 5/2002 | Moller | |
| 2002/0120235 A1 | 8/2002 | Enggaard | |
| 2003/0050609 A1* | 3/2003 | Sams | A61M 5/31551 604/208 |
| 2004/0059299 A1 | 3/2004 | Moller | |
| 2004/0097883 A1 | 5/2004 | Atterbury | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2005/0267403 A1* | 12/2005 | Landau | A61M 5/30 604/70 |
| 2006/0153693 A1 | 7/2006 | Fiechter et al. | |
| 2007/0016143 A1 | 1/2007 | Miller et al. | |
| 2009/0254043 A1* | 10/2009 | Van Bulow | A61M 5/24 604/207 |
| 2009/0275916 A1 | 11/2009 | Harms et al. | |
| 2013/0313823 A1 | 11/2013 | Holmqvist | |
| 2014/0236096 A1 | 8/2014 | Helmer et al. | |
| 2015/0038917 A1 | 2/2015 | Nielsen | |
| 2016/0129196 A1* | 5/2016 | Hirschel | A61M 5/31541 604/211 |

FOREIGN PATENT DOCUMENTS

| | | |
|---|---|---|
| CN | 101500630 | 8/2009 |
| CN | 102076372 | 5/2011 |
| CN | 103492001 | 1/2014 |
| CN | 104220113 | 12/2014 |
| CN | 105451794 | 3/2016 |
| EP | 0496141 | 7/1992 |
| EP | 0897729 | 2/1999 |
| EP | 0937471 | 8/1999 |
| EP | 0937476 | 8/1999 |
| EP | 1516638 | 3/2005 |
| EP | 1776975 | 4/2007 |
| EP | 2525851 | 11/2012 |
| EP | 2185227 | 3/2014 |
| GB | 0304822.0 | 3/2003 |
| GB | 0304823.8 | 11/2017 |
| JP | 2009-540986 | 11/2009 |
| JP | 2015-516201 | 6/2015 |
| WO | WO 93/07922 | 4/1993 |
| WO | WO 93/24160 | 12/1993 |
| WO | WO 1999/038554 | 8/1999 |
| WO | WO 2001/010484 | 2/2001 |
| WO | WO 02/030495 | 4/2002 |
| WO | WO 02/092153 | 11/2002 |
| WO | WO 03/080160 | 10/2003 |
| WO | WO 2004/078239 | 9/2004 |
| WO | WO 2004/078240 | 9/2004 |
| WO | WO 2004/078241 | 9/2004 |
| WO | WO 2006/084876 | 8/2006 |
| WO | WO 2008/003560 | 1/2008 |
| WO | WO 2009/022132 | 2/2009 |
| WO | WO 2009/132777 | 11/2009 |
| WO | WO 2011/089207 | 7/2011 |
| WO | WO 2012/105892 | 8/2012 |
| WO | WO 2012/110583 | 8/2012 |
| WO | WO 2012/171981 | 12/2012 |
| WO | WO 2013/153011 | 10/2013 |
| WO | WO 2013/156350 | 10/2013 |
| WO | WO-2013153011 A1 * | 10/2013 |
| WO | WO 2014/116905 | 7/2014 |
| WO | WO 2015/010215 | 1/2015 |
| WO | WO 2015/018811 | 2/2015 |
| WO | WO 2015/032455 | 3/2015 |

OTHER PUBLICATIONS

International Search Report and Written Opinion in International Application No. PCT/EP2016/056102, dated May 10, 2016, 8 pages.

(56) References Cited

OTHER PUBLICATIONS

International Preliminary Report on Patentability in International Application No. PCT/EP2016/056102, dated Sep. 26, 2017, 6 pages.

* cited by examiner

A-A

B-B

HOUSING FOR AN INJECTION DEVICE AND INTERCONNECTION OF HOUSING COMPONENTS

CROSS REFERENCE TO RELATED APPLICATIONS

The present application is the national stage entry of International Patent Application No. PCT/EP2016/056102, filed on Mar. 21, 2016, and claims priority to Application No. EP 15160252.1, filed on Mar. 23, 2015, the disclosures of which are expressly incorporated herein in entirety by reference thereto.

TECHNICAL FIELD

The present disclosure relates to a housing for an injection device for delivery of a liquid medicament. In one aspect the disclosure relates to elongated or tubular housing components for an injection device and to a non-releasable interconnection of housing components. The disclosure particularly relates to a positive and permanent connection of housing components, wherein each housing component prior to mutual assembly accommodates particular components of the injection device, such as a cartridge and a drive mechanism, respectively.

BACKGROUND

Injection devices for setting and dispensing single or multiple doses of a liquid medicament are well-known in the art. Generally, such devices have a substantially similar purpose to that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

Disposable injection devices, e.g. of pen-injector type, having an elongated housing extending with a long axis in an axial direction typically comprise at least two substantially tubular-shaped housing components that need to be interconnected to form a rigid joint at the end of a automated assembly and manufacturing process. Typically, a distal housing component, commonly denoted as a cartridge holder and configured to accommodate a cartridge filled with the medicament as well as a proximal housing component, commonly denoted as a body to accommodate a drive mechanism operably engaging with a piston of the cartridge need to be mutually connected to form an irreleasable and permanent connection. For a rather efficient and reliable mass manufacturing of such injection devices it is desirable to provide a positive interconnection of the at least two housing components of the injection device without the aid of adhesives or without welding that would require application of thermal energy.

Document WO 2012/105892 A1 discloses for instance a coupling arrangement in a medicament delivery device. The coupling arrangement is adapted to permanently attach a first and a second longitudinally elongated tubular component to each other. The coupling arrangement comprises first positive connection means configured to lock the first and the second components to each other such that the components are locked from being moved in a longitudinal direction in relation to each other. The coupling arrangement further comprises a second positive connection means configured to lock the first and the second component to each other such that the components are locked from being rotated in relation to each other about a longitudinal axis of the components.

SUMMARY

The present disclosure provides a permanent and irreleasable connection of two housing components for an injection device such like a pen-type injector, which housing components provide easy and straight forward mutual assembly. It is a further aim, that the housing components form a rigid and tight long-term stable positive interconnection when mutually assembled to form a housing of an injection device. The interconnection should be highly resistant to mechanical loads and should be able to withstand mechanical shock that may for instance inadvertently arise in the event that the injection device drops to the ground. Furthermore, the interconnection of the housing components should be substantially free of clearance to enhance the quality feel of the injection device.

In a first aspect of the disclosure an elongated housing for an injection device configured for delivery of a liquid medicament is provided. The elongated housing is typically of substantially tubular shape. Its long axis extends in an axial direction or defines an axial direction. A distal axial direction points towards an injection site when in use while a proximal end of the device is actuatable by a user or patient. The distal end of the elongated housing is the end section where the liquid medicament is actually dispensed during use of the device whereas an opposite proximal end section is typically equipped with a dose dial and/or with a dose button providing dose setting and dose dispensing functionalities to be conducted by a user of the injection device.

The elongated housing comprises a tubular-shaped cartridge holder to accommodate a cartridge filled with the medicament. The tubular-shaped cartridge holder comprises a proximal connecting end and forms a distal housing component of the elongated housing. The elongated housing further comprises a proximal housing component denoted as a body. The body is configured to accommodate or to receive a drive mechanism of the injection device, which drive mechanism is operably engageable with a piston of the cartridge located inside the cartridge holder. The body as a proximal housing component comprises a distal connecting end connectable to the proximal connecting end of the cartridge holder. Typically, the proximal connecting end and the distal connecting end are interconnectable in an interleaved or in an at least partially nested way. In an assembly or connection arrangement at least portions of the proximal connecting end and the distal connecting end mutually overlap and mechanically engage to form the desired interconnection of the two housing components, namely of the cartridge holder and of the body.

One of the proximal connecting end and the distal connecting end comprises an insert section which may be stepped down in radial direction. The other one of the proximal connecting end and the distal connecting end comprises a receptacle to axially receive the insert portion. Hence, the inner diameter of the receptacle matches with the outer diameter of the insert portion so that the insert portion is axially insertable into the receptacle to form the interconnection of cartridge holder and body.

Typically, the cross-section and geometric shapes of the receptacle and of the insert portion mutually match in such a way, that a positive interconnection of receptacle and insert portion can be obtained.

The insert section comprises at least one fastening element to positively engage with a complementary-shaped fastening element of the receptacle. Mutually engageable and complementary-shaped fastening elements of the insert section and the receptacle provide an axial interlock of cartridge holder and body. Typically, the insert section is slidably displaceable inside the receptacle until the mutually corresponding fastening elements of insert section and receptacle engage. Once the fastening elements of insert section and receptacle engage the insert section is axially fixed to the receptacle. Hence, upon mutual engagement of fastening elements of the insert section and the receptacle the cartridge holder is axially fixed to the body and vice versa.

The mutually corresponding fastening elements of the insert section and the receptacle comprise at least one pair of a radial protrusion mating with a radial recess provided on an inside wall of the receptacle and on an outside wall of the insert section. Typically, the at least one radial protrusion comprises a slanted or beveled edge so as to form a wedge-shaped geometry as seen in an insertion direction. Moreover, the receptacle and the protrusion comprise mutually engaging and complementary-shaped abutments section facing in an axial direction, which abut as the fastening position of the insert section inside the receptacle has been reached.

Typically, there are provided several pairs of fastening elements on the outside wall of the insert section and on the inside wall of the receptacle. As seen in a circumferential direction the fastening elements of the receptacle and of the insert section are located at well-defined angular positions. This requires that the insert section is inserted into the receptacle in at least one particular angular orientation with regard to the long axis of insert section or receptacle as an axis of rotation. For this there may be provided additional positively engaging guiding means defining and retaining a predefined angular orientation of insert section and receptacle prior to and during insertion of the insert section into the receptacle in an axial direction.

Furthermore, a radial depth of the radial recess in one of the inside wall of the receptacle or the outside wall of the insert section is smaller than a thickness of the respective sidewall of the insert section or of the receptacle. Hence, the radial recess is configured in form of a blind hole or pocket hole but does not feature a through opening in the sidewall of insert section or receptacle. In this way the radial recess could be formed on an inside-facing portion of the sidewall of the receptacle. It would not be visible from outside the device. Apart from that a limited depth of the radial recess is beneficial in terms of the mechanical stability of the respective sidewall section. Implementation of a radial recess with a radial depth smaller than the thickness of the sidewall in which the radial recess is located makes the respective housing component less susceptible to mechanical failure or fracture.

In another embodiment the insert section is axially confined or axially delimited by a radially outwardly extending flange section. The insert section typically comprises or forms a socket portion with an outer diameter that is at least slightly smaller than the outer diameter of the flange section. Hence, the outer diameter of the insert section is smaller than the diameter of the axially adjacent flange section. The flange section therefore axially confines the stepped down insert section of one of the cartridge holder and body.

In another embodiment a sidewall of the receptacle comprises a beveled axial end face that is complementary-shaped to a beveled abutment face of the flange section. The beveled axial end face of the receptacle's sidewall forms an axial edge or axial end of the receptacle and faces towards the abutment face of the flange section of the insert section. The beveled axial end face and the beveled abutment face of the receptacle and of the flange section define an axial abutment of the cartridge holder and the body so as to limit an insert motion of the insert section entering the receptacle. By means of beveled faces the mutual abutment of the sidewall of the receptacle of cartridge holder or body and the correspondingly-shaped flange section of body or cartridge holder inherently provides a tolerance compensation.

Typically, cartridge holder and body are made of injection molded plastic components that are inevitably subject to geometric tolerance variation. Providing beveled and complementary-shaped end faces and abutment faces on the receptacle and the flange section allows these abutment faces to pass over each other, with the Body splaying radially outwards. Causing the Body to splay radially outwards in this way requires a reduced force and stress, when compared to a joint formed with abutment faces that face in a direction perpendicular to the direction of assembly, for a given over-travel once the abutment faces first make contact. This facilitates a tight axial engagement to be provided over comparatively large geometric tolerance margins, without over stressing the components or requiring excessive assembly force during the final assembly step of interconnecting cartridge holder and body.

By means of the beveled axial end face at the longitudinal edge of the receptacle it is possible to induce a radially outwardly directed splaying or an at least slight radial widening of the receptacle which may be of further advantage to reduce friction between the interior of the receptacle and an outer surface of the insert section. Also in this way assembly forces may be effectively reduced and assembly of cartridge holder and body can be facilitated.

According to another embodiment the end face of the receptacle and the abutment face of the flange section are facing in opposite axial directions. When the insert section reaches a fastening position inside the receptacle the beveled abutment face of the flange section and the beveled axial end face of the sidewall of the receptacle are in mutual abutment. On a microscopic scale the fastening position of the insert section inside the receptacle may vary within inevitable geometric tolerance margins that arise from the production and manufacturing of the individual housing components, cartridge holder and body. By having complementary-shaped beveled end faces and abutment faces on the sidewall of the receptacle and on the flange section, respectively such geometric tolerances can be easily compensated. Typically, for all tolerance-based variable axial fastening positions of the insert section inside the receptacle a mutual abutment of the beveled end face the beveled abutment face is always obtainable. In this way a rather rigid, tight and slack-free interconnection can be formed between cartridge holder and body, which is rather insensitive to the geometric tolerances of cartridge holder and body.

The fastening elements of the insert section and of the receptacle are located and arranged in such axial positions relative to the beveled axial end face and the beveled abutment face so that the complementary-shaped fastening elements of insert section and receptacle just engage when the abutment face of the flange section actually gets in abutment or is already in abutment with the beveled end face of the sidewall of the receptacle. Typically, an abutment configuration of the end face and the abutment face is obtained even prior to the irreleasable engagement of the fastening elements of the receptacle and the insert section. In this way it is somewhat guaranteed, that the beveled axial end face and the beveled abutment face are in rigid or tight abutment as the complementary-shaped fastening elements of insert section and receptacle interconnect or get mutually interlocked.

In another embodiment one of the insert section and the receptacle comprises an axially extending radial slot. The radial slot comprises an axially elongated recessed portion that extends from an axial edge of the sidewall of the insert section towards the flange section. When implemented on the inside of the receptacle the slot extends axially from the beveled axial end face of the receptacle in axial direction. The other one of the insert section and the receptacle then comprises a radial protrusion or an axially extending radial rib complementary-shaped to the axially extending radial slot. When at least the radial slot extends in axial direction mutually engaging radial rib and radial slot define a rotational interlock of receptacle and insert section.

Moreover, the radial slot and the complementary-shaped protrusion or rib define at least one or only a few relative angular positions of insert section and receptacle that allow and support a sliding insertion of the insert section into the receptacle. In this way, a pair formed by the axially extending slot with the protrusion or with the axially extending rib establishes a rotational interlock for the insert section and the receptacle. The rib and the slot have to engage prior to or during insertion of the insert section into the receptacle and prior to a mutual engagement of the fastening elements of receptacle and insert section forming a second axial interlock of insert section and receptacle.

Along the circumference of the inside of the receptacle and along the outside of the insert section there may be provided several mutually corresponding fastening elements as well as several mutually corresponding slots and protrusions or ribs. In this way, any mechanical loads acting between the insert section and the receptacle may divide and may be spread over numerous mutually engaging fastening elements or mutually engaging axially extending slots or ribs.

The mutually corresponding fastening elements of insert section and receptacle to form an axial interlock between the cartridge holder and the body are typically symmetrically or equally spaced along the inner and outer circumference of the receptacle and the insert section. In this way, any mechanical load to be transferred between cartridge holder and body in axial direction may somewhat equally split over the pairs of mutually engaging fastening elements of insert section and receptacle. Any rotational forces with regard to a rotation axis extending longitudinally through the cartridge holder or body may be transferred via the radial protrusion or radial rib located inside the at least one radial slot of insert section and receptacle of cartridge holder and body, respectively.

When providing more than one axially extending radial slot the at least two or even more slots could be equally spaced along the inner circumference of the receptacle or outer circumference of the insert section. In this way any relative angular momentum acting between the cartridge holder and body could be somewhat equally transferred via the interface of insert section and receptacle. However, it is also conceivable to implement a symmetry breaking feature by having only one axial slot to engage with a complementary-shaped radial protrusion or rib. Alternatively it is conceivable, that the angular position of the at least two axially extending slots is asymmetric so that the angular position of the radial slots defines a unique relative angular position of cartridge holder and body, in which the insert is axially insertable into the receptacle.

According to another embodiment the axially extending radial slot and the axially extending rib are mutually axially insertable free of clearance. In this way the mutual engagement of the slot and the rib already provides a slack-free arrangement of cartridge holder and body during an insert motion of the insert section into the receptacle. This helps to improve the quality feel of the device. Moreover, a complementary geometric configuration of the axially extending radial slot and the axially extending radial rib free of clearance helps to improve the accuracy at which a label is to be applied to the outside of the body or cartridge holder. For an automated label attachment to at least one of the cartridge holder and body the other one of cartridge holder and body will be gripped or fixed in an automated assembly process while the cartridge holder or body is subject to an attachment of a label thereto. By means of a clearance-free geometric design of axially extending slot and rib on the inside of the receptacle and on the outside of the insert portion a rather rigid and positionally stable configuration of cartridge holder and body can be obtained even before the fastening elements of insert section and receptacle mutually engage thereby forming the axial interlock.

According to another embodiment it is the insert section that forms the proximal connecting end of the cartridge holder and it is the receptacle that forms the distal connection end of the body. Consequently, the beveled axial end face is located on a distal end of the body and the beveled abutment face of the flange section is provided on the cartridge holder. It forms a proximal end of the insert section of the cartridge holder. In a final assembly configuration the beveled axial end face of the sidewall of the receptacle faces in a distal direction whereas the beveled abutment face of the flange section of the cartridge holder faces in the opposite proximal direction.

Typically, the outer diameter of the flange section substantially matches with the outer diameter of the receptacle so that the interconnection and mutual abutment of the flange section and the sidewall of the receptacle is substantially flush. Having the insert section located on a proximal end of the cartridge holder and having the receptacle on a distal end of the body is beneficial in that the body may comprise a slightly larger diameter than the cartridge holder. This is of particular advantage to accommodate numerous mechanically interacting components of the drive mechanism inside the body. Moreover, by having the insert section located on the proximal end of the cartridge holder the diameter of the cartridge holder can be easily reduced compared to the diameter of the body. This is of particular use when cartridges of limited or reduced diameter should be used with the injection device. Diameter reduced cartridges may be particularly useful for administering and for delivery of rather small or of a non-integer number of doses of the medicament as for instance measured in International Units (IU).

In another embodiment the at least one fastening element of the receptacle comprises the radial protrusion and the at least one fastening element of the insert section comprises the radial recess. Implementing the radial recess or radial recesses on the insert section is beneficial in terms of bending loads that apply during the insertion of the insert section into the receptacle. When bending loads are applied across the joint, having the radial protrusions extending radially inwardly from an inside facing sidewall of the receptacle and having the complementary-shaped radial recesses to extend radially inwardly on the outside facing sidewall of the insert section leads to a circumferentially directed compressive stress in the insert section and to a circumferentially directed tensile stress in the sidewall of the receptacle. Since thermoplastic materials are more susceptible to failure via tensile stress than compressive stress it is beneficial to arrange the radial recesses on or in the insert section of the cartridge holder and to have the radial protrusions on the inside facing surface of the receptacle of the body. For the same reasons it is also beneficial that the at least one axially extending radial slot is located on the outside of the insert section of the cartridge holder and that the complementary-shaped at least one radial protrusion or axially extending radial rib is provided on an inside facing portion of the receptacle of the body.

It is generally of particular benefit, that any structural weakening elements, such like radial recesses or axially extending radial slots are placed on the cartridge holder, where stresses are of compressive type and that protrusions and ribs radially protruding from a sidewall portion are placed on the body, where stresses are of tensile type.

According to another embodiment an axial distance d1 between the at least one fastening element of the receptacle and the axial end face is larger than or equal to an axial distance d2 between the at least one fastening element of the insert section and the abutment face of the flange section thereof. In this way it is guaranteed, that the beveled axial end face of the sidewall of the receptacle axially engages with the complementary-shaped beveled abutment face of the flange section of the insert section as the mutually corresponding fastening elements of the receptacle and the insert section engage to form an axial interlock of cartridge holder and body. The difference between the distances d1 and d2 is fairly small. The difference between said distances d1 and d2 is in the submillimeter range. It may be as small as a few, a few tens or hundreds of micrometers.

The difference between the axial distances d1 and d2 is substantially equal to the maximum tolerance margin of the position of the fastening element, the complementary-shaped beveled abutment face and axial end face of the flange section and of the sidewall of the receptacle, respectively. So even in the loosest axial tolerance conditions of insert section and receptacle and their respective mutually corresponding fastening elements a zero axial play or slack between cartridge holder and body can be obtained. By means of the beveled abutment face of the flange section and the complementary-shaped beveled axial end face of the receptacle axial interference and axial geometric tolerances of insert section and receptacle can be absorbed through elastic and radially directed deformations to always enable axial engagement of the fastening elements.

By means of the beveled flange and beveled end face the body is enabled to overtravel past its nominal position relative to the cartridge holder during mutual assembly. Depending on the shape and configuration of the complementary-shaped beveled flange and beveled end face the side wall of the receptacle may be subject to splay radially outwardly. Such a radial splaying requires significantly less forces and less energy compared to a configuration where the contact surfaces of the flange section and the receptacle were not angled and wherein all of the axial interference would have to be accommodated with axial compression. Additionally, also the insert section of the cartridge holder may be subject to splay radially inwardly as compressive forces apply across the interface of mutually engaging beveled surfaces.

The beveled or angled profiles of the flange section and the axial end face of the receptacle also prevent or at least reduce a leverage effect from increasing the axial load on the fastening elements during application of bending loads to the device. In addition, the radially outwardly directed splaying of the receptacle of the cartridge holder during a final step of inserting the insert section into the receptacle may also help to establish a mutual engagement of the fastening elements. Typically, the fastening elements are configured as snap features, wherein the radial protrusion comprises a wedge-shaped profile as seen in axial direction.

According to a further embodiment the beveled axial end face and the beveled abutment face are shaped to generate a radially inwardly directed load to the insert section when the beveled axial end face and the beveled abutment face are subject to an axial compression.

Likewise, and according to another embodiment the beveled axial end face and the beveled abutment face of the receptacle and the flange section are shaped to generate a radially outwardly directed load to the receptacle when subject to an axial compression thereby splaying the sidewall thereof radially outwardly.

Radially outwardly directed load to the receptacle and radially inwardly directed load to the insert section also helps to establish the snap fit connection of the mutually corresponding fastening elements of the receptacle and the insert section. In addition, eventual point loads that may be present in the interface of mutually engaging fastening elements of the insert section and the receptacle may be reduced due to the mutual abutment of the beveled axial end face and the beveled flange section. The total surface of mutually engaging flange section and beveled end face of the receptacle is substantially larger than the mutually engaging abutment sections of the fastening elements. An axial compression and mechanical stress across the interface of cartridge holder and body can be equally and smoothly distributed across the comparatively large surfaces of the beveled axial end face and the beveled flange section of the sidewall of the receptacle and the insert section, respectively.

According to another embodiment, at least one of the axial end face of the sidewall of the receptacle and the flange section of the insert section comprises an axially protruded portion to mate with a complementary-shaped axial recessed portion of the other one of the axial end face and the flange section. In this way, the interface of axial end face and flange section is provided with a symmetry breaking feature that defines a specific orientation of the cartridge holder relative to the body with regard to a longitudinal axis of rotation. The protruded portion may be provided on the flange section and may extend in proximal direction, hence towards the body. Correspondingly, the body comprises an axially recessed portion on its distal and beveled end face to receive and to engage with the protruded portion of the flange section.

By means of the axially protruded portion and the complementary-shaped axially recessed portion the symmetry breaking feature of cartridge holder and body is immediately recognizable from outside the housing component's cartridge holder and body. Moreover, by means of the axially protruded portion and the complementary-shaped axially recessed portion the housing may be provided with a function-specific design.

In another embodiment the insert section comprises a free axial end section and an intermediate section located axially between the free axial end section and the flange section. Here, the diameter of the free axial end section is smaller than the diameter of the intermediate section. Complementary, also the receptacle comprises a free axial end section and an axially adjacently located intermediate section. At least the intermediate section of the receptacle is complementary-shaped to the axial end section of the insert section. In this way, the cartridge holder and the body each comprise a stepped wall portion, wherein the respective faces of the matching stepped wall portions are in radial contact and in radial abutment when the body and the cartridge holder are fully assembled.

At least the outer diameter of the axial end section of the insert section closely matches with the inside surface and inner diameter of the intermediate section of the receptacle. When fully assembled the faces of the axial end section of the insert section and of the intermediate section of the receptacle are somewhat in close mechanical contact. They may even form almost a press fit. This allows the joint and interface of cartridge and body to tolerance greater radial misalignment during assembly while still maintaining a small draft angle and maintaining radial contact in a fully assembled condition. In addition it is also conceivable, that the intermediate section of the insert section and the axial end section of the receptacle mutually match to get in close radial contact when the cartridge holder and the body are in a final assembly configuration.

In another aspect the disclosure relates to an injection device for delivery of a liquid medicament. The injection device comprises a housing as described above and further comprises a drive mechanism arranged inside the body and fixed to the body. Typically, the injection device is of pen-injector type and allows a user to individually set a dose of variable size and to dispense and to inject the dose into biological tissue.

In another embodiment the injection device further comprises a cartridge arranged inside the cartridge holder of the housing, wherein the cartridge holder and the body are irreleasably connected. In this way the injection device is of disposable type. Due to the irreleasable connection of cartridge holder and body, which is typically obtained only by way of a positive interlock of mutually corresponding fastening elements of the insert section and the receptacle the entire injection device is intended to be discarded when the content of the cartridge has been used up. Disconnecting of cartridge holder and body is only possible by an at least partial destruction or disruption of one of these housing components.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N—(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39), des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two p sheets create a "sandwich" shape, held together by interactions between conserved cysteines and other charged amino acids.

There are five types of mammalian Ig heavy chain denoted by a, 5, E, y, and p. The type of heavy chain present defines the isotype of antibody; these chains are found in IgA, IgD, IgE, IgG, and IgM antibodies, respectively.

Distinct heavy chains differ in size and composition; a and y contain approximately 450 amino acids and 5 approximately 500 amino acids, while p and E have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains y, a and b have a constant region composed of three tandem Ig domains, and a hinge region for added flexibility; heavy chains p and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by A and K. A light chain has two successive domains: one constant domain (CL) and one variable domain (VL). The approximate length of a light chain is 211 to 217 amino acids. Each antibody contains two light chains that are always identical; only one type of light chain, K or A, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present disclosure without departing from the spirit and scope of the disclosure. Further, it is to be noted, that any reference numerals used in the appended claims are not to be construed as limiting the scope of the disclosure.

BRIEF DESCRIPTION OF THE FIGURES

In the following, an embodiment of the disclosure is described in detail by making reference to the drawings, in which.

DETAILED DESCRIPTION

Figure 7:
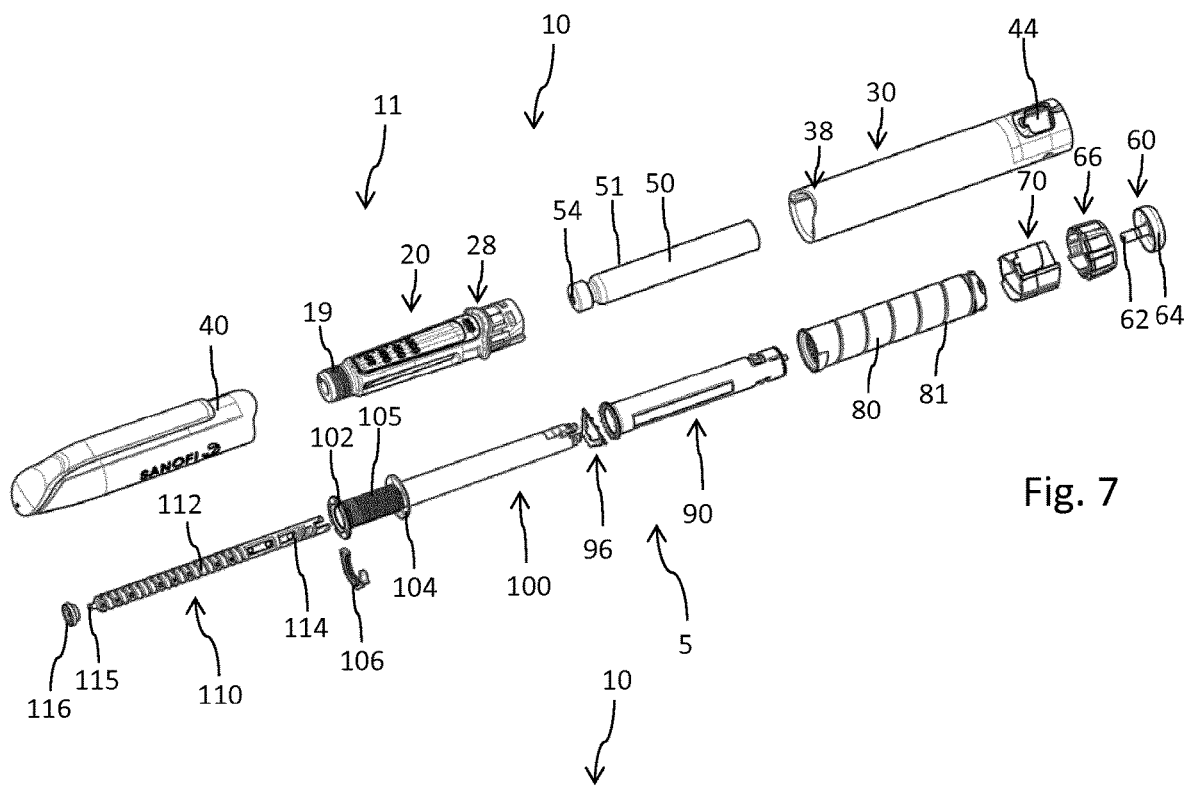
FIG. 7 is an exploded view of the components of the injection device and FIG. 8 shows a longitudinal cross-section through the injection device according to FIG. 7.
Figure 8:
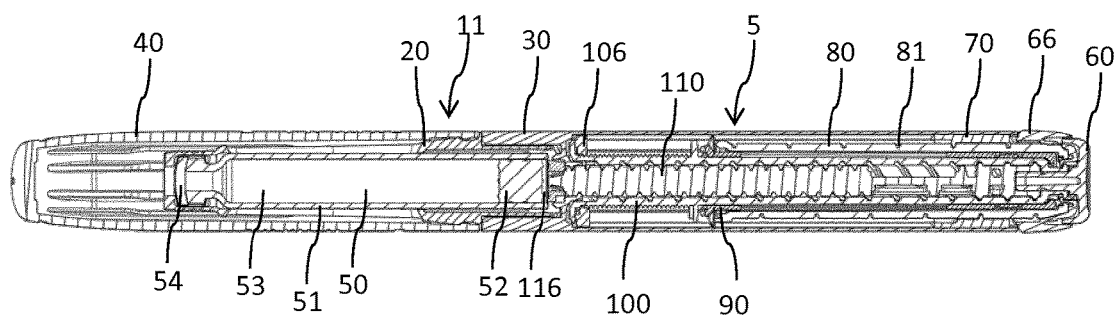

The injection device 10 as shown in FIGS. 7 and 8 is configured as a pen-type injector. It comprises an elongated housing 11 extending in a longitudinal or axial direction. Towards a distal direction 1 the injection device 10 comprises a distal housing component denoted as cartridge holder 20. In the opposite longitudinal direction the housing 11 comprises a second housing component denoted as body 30. Both housing components, namely cartridge holder 20 and body 30 are of tubular and elongated shape. The cartridge holder 20 is configured to accommodate a cartridge 50 comprising a tubular-shaped barrel 51 and being filled with a liquid medicament 53. At a distal end the cartridge 50 comprises a pierceable seal 54 typically comprising a pierceable septum of an elastomeric material.

At the opposite proximal end the cartridge 50 is sealed by a piston 52 slidably arranged inside the barrel 51 of the cartridge 50. For dispensing of a dose of the liquid medicament 53 the cartridge holder 20 comprises a threaded socket 19 at its distal end to receive a correspondingly threaded needle assembly with a double-tipped injection needle. A proximal tipped end of the injection needle of the needle assembly, which is presently not illustrated, is configured to pierce the distal seal 54 of the cartridge 50 thereby gaining access to the interior of the cartridge 50. The distal end of the injection needle is then configured to puncture biological tissue to deliver the medicament. For medicament delivery the piston 52 is to be displaced in distal direction 1 under the action of a distally advancing piston rod 110 of a drive mechanism 5 of the injection device 10. The drive mechanism 5 is accommodated and fixed in the body 30 of the injection device 10.

The cartridge holder 20 and the body 30 are to be interconnected by means of a positive connection as it is explicitly shown in FIGS. 1-6. The cartridge holder 20 comprises a proximal connecting end 21 to irreleasably interconnect with a distal connecting end 31 of the body 30. The cartridge holder 20 and the body 30 are interconnectable in an interleaved or nested way. In the presently illustrated embodiment the proximal connecting end 21 of the cartridge holder 20 comprises a stepped down insert section 22 which is axially confined in distal direction 1 by a radially outwardly extending flange section 23. The distal connecting end 31 of the body 30 comprises a receptacle 32 to axially receive the insert section 22 of the cartridge holder 20. The outer diameter of the insert section 22 exactly matches with the inner diameter of the receptacle 32 so that the insert section 22 can be inserted into the receptacle 32 by means of a sliding motion in proximal direction 2 relative to the body 30.

The sidewall 33 of the receptacle 32 comprises a beveled axial end face 34 that forms a distal end of the body 30. The flange section 23 comprises a complementary-shaped beveled abutment face 24 featuring a geometric shape that matches with the shape of the beveled axial end face 34 of the sidewall 33. As it is shown in FIG. 5 the beveled abutment face 24 faces in proximal direction 2 whereas the beveled axial end face 34 faces in distal direction 1.

Figure 4:
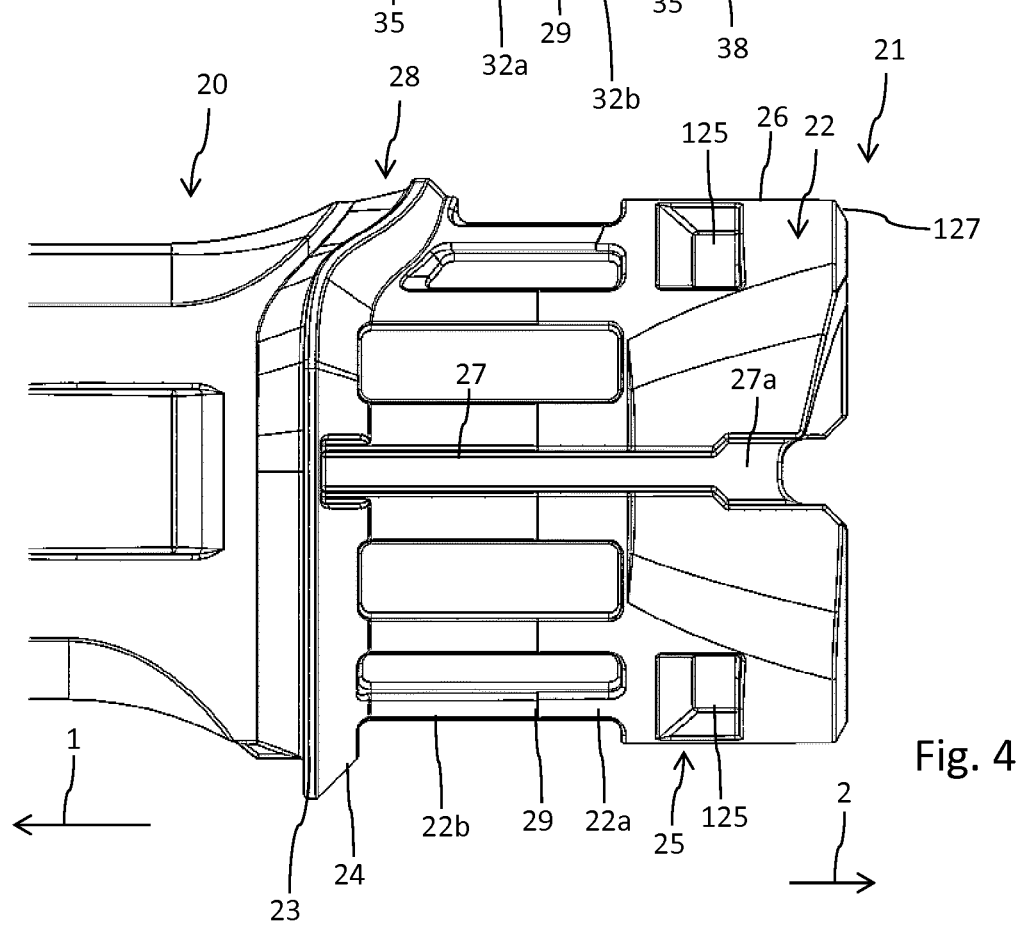
FIG. 4 is a side view of the proximal connecting end of the cartridge holder.
Figure 5:
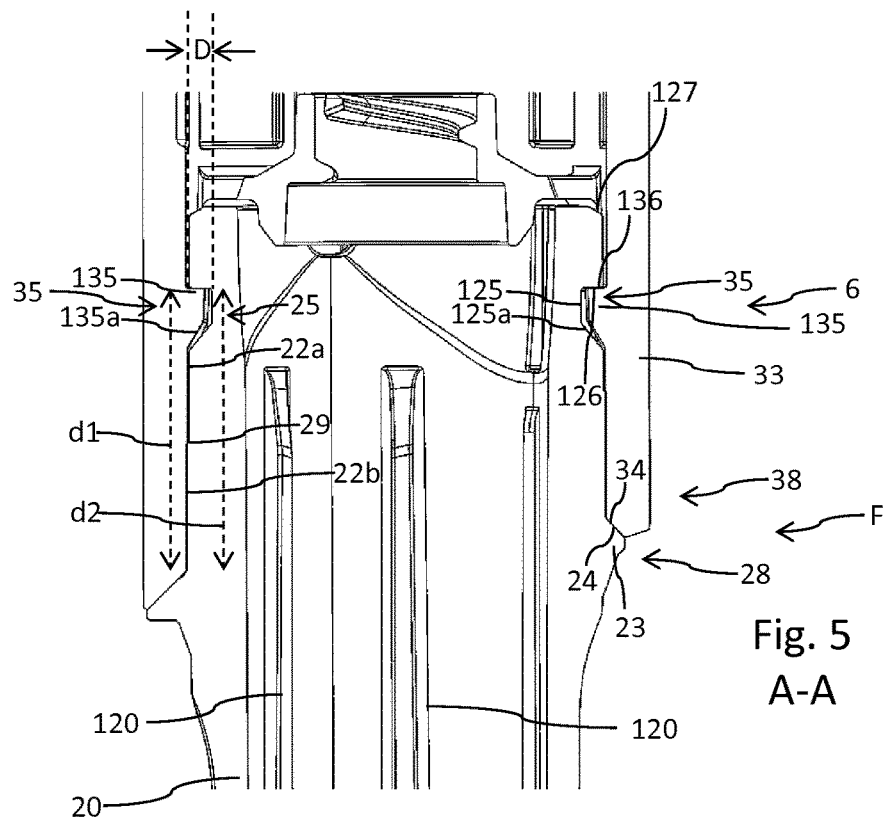
FIG. 5 is a longitudinal cross-section through the cartridge holder connected to the body along A-A according to FIG. 1.
Figure 6:
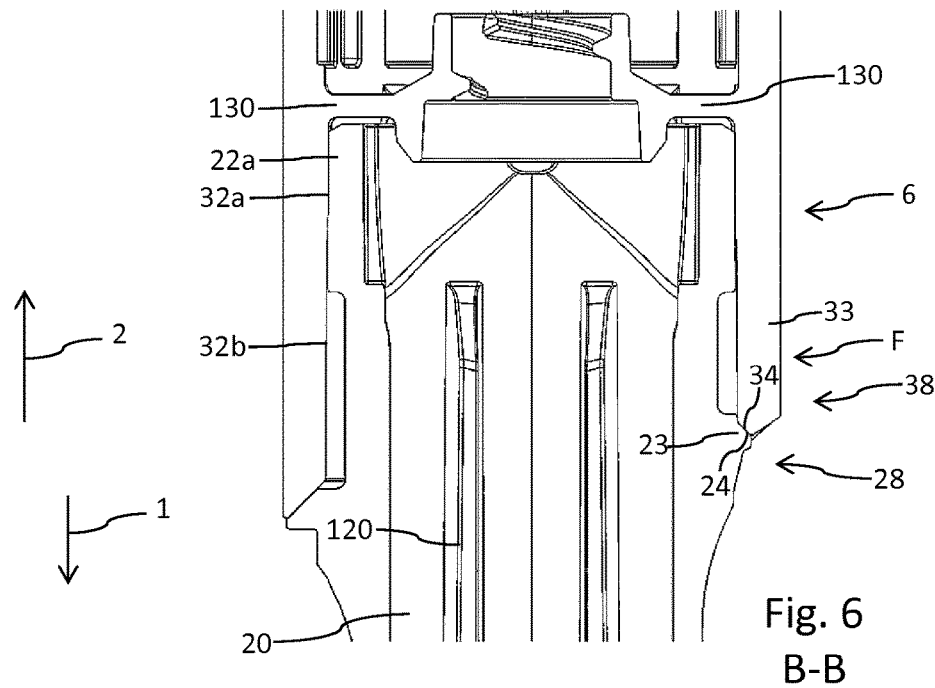
FIG. 6 is a further longitudinal cross-section through the interface along B-B of FIG. 1.

In order to irreleasably interconnect the cartridge holder 20 and the body 30 in a final assembly or final fastening position F as shown in FIGS. 5 and 6 there are provided mutually corresponding fastening elements 35 and 25 on the inside of the receptacle 32 and on the outside of the insert section 22. In the embodiment as illustrated in FIGS. 1-6 the body 30 comprises various fastening elements 35 radially inwardly extending from the inside of the sidewall 33 of the receptacle 32.

There are provided four fastening elements 35 arranged along the inner circumference of the sidewall 33 of the receptacle 32. The fastening elements 35 are arranged near a flange-like threaded support 130 having a central through opening 131 through which the threaded piston rod 110 extends. The support 130 extends substantially perpendicular to the axial direction and confines the receptacle 32 in the proximal direction if the abutment face 24 and the end face 34 travel over each other by a sufficient distance. The support 130 effectively divides the body 30 into a distal interface section formed by the receptacle 32 and a proximal section to accommodate the mechanical components of the drive mechanism 5.

The fastening elements 35 provided on the inside of the sidewall 33 of the receptacle 32 comprise radially inwardly extending protrusions 135 having a beveled section 135a facing in distal direction and extending radially inwardly from the sidewall 33 to the crest of the protrusion 135. The protrusion 135 terminates in proximal direction 2 with a stepped down abutment section 136 that extends radially outwardly from the crest of the protrusion 135 and which ends at the inside of the sidewall 33.

The fastening element 25 of the cartridge holder is complementary-shaped to the fastening element 35 of the body 30. It comprises a radially extending recess 125 terminated in proximal direction 2 by a radially extending abutment section 126. The recess 125 also comprises a beveled section 125a to accommodate the correspondingly-shaped beveled section 135a of the protrusion 135 when cartridge holder 20 and body 30 are arranged in a final assembly configuration or fastening position F. Then an axial interlock 6 between the fastening elements 25, 35 and hence between cartridge holder 20 and body 30 is attained.

The proximal end of the cartridge holder 20 comprises a beveled edge 127 at its outer circumference that engages with the beveled section 135a of the protrusion 135 as the insert section 22 is moved in the proximal direction 2 into the receptacle 32. The beveled edge 127 facilitates mutual assembly and induces an elastic deformation of both, the sidewall 33 of the receptacle 32 and of the insert section 22. The mutually corresponding fastening elements 25, 35 of cartridge holder 20 and body 30 are subject to tensile stress and to compressive stress during insertion of the insert section 22 into the receptacle 32. Since the outer diameter of the insert section 22 matches with the inner diameter of the receptacle 32 an insert and fastening procedure requires elastic deformation of the housing component's cartridge holder 20 and body 30 due to the shape of the mutually corresponding fastening elements 25, 35. The housing components, cartridge holder 20 and body 30 that are typically single pieced and are made by way of injection molding of a thermoplastic material.

During mutual assembly, the receptacle 32 and its sidewall 33 experiences a radially outwardly directed load or stress leading to tensile forces in circumferential direction inside the sidewall 33. Correspondingly, the insert section 22 experiences a radially inwardly directed pressure leading to compressive stress in a circumferential direction inside the insert section 22. Since thermoplastic materials are more sensitive to tensile than to compressive stress it is of particular benefit, that a weakening recessed structure in form of the recesses 125 is provided in the insert section 22 of the cartridge holder 20. The radially inwardly extending protrusions 135 of the fastening elements 35 of the body 30 also provide a structural reinforcement so that the sidewall 33 in the region of the fastening elements 35 is less susceptible in response to tensile loads that may arise during an assembly procedure.

The recesses 125 provided in the insert section 22 of the cartridge holder 20 are configured as blind holes or pocket holes and do not completely intersect the wall structure of the insert section 22. Hence, a radial depth D of the recesses 125 is smaller than the thickness of the sidewall of the insert section 22. Making use of such blind recesses 125 instead of through openings also enhances and improves the mechanical stability and resistivity against mechanical loads present on the respective fastening element 25 during assembly. As a result a rather rigid, tight and long-term mechanically stable irreleasable connection of cartridge holder 20 and body 30 is provided.

The fastening elements 25 are provided on an outside wall 26 of the insert section 22 whereas the corresponding fastening elements 35 are provided on an inside wall 36 of the sidewall 33 forming the receptacle 32.

Once a final assembly configuration and hence a fastening position F has been reached the abutment section 136 of the protrusions 135 facing in proximal direction 2 are in direct abutment with the distally facing abutment sections 126 of the recesses 125, wherein the abutment sections 126 face in distal direction 1. At the same time the proximally facing beveled abutment face 24 of the flange section 23 of the cartridge holder 20 is in direct abutment with the complementary-shaped beveled distal end face 34 of the sidewall 33 of the body 30. In this way even a kind of an axial clamping of cartridge holder 20 and body 30 can be obtained.

Moreover, an axial distance d1 between the fastening element 35 and the distal beveled axial end face 34 of the receptacle 32 is larger than or equal to an axial distance d2 between the at least one fastening element 25 of the insert section 22 and the abutment face 24 of the flange section 23. It is even of particular benefit when the axial distance d1 is slightly larger than the axial distance d2. In this way it is somewhat guaranteed, despite manufacturing variation, that the complementary-shaped beveled faces 34, 24 are in tight axial engagement before or at the point that the mutually corresponding fastening elements 25, 35 engage. The shape of the complementary-shaped beveled faces 24, 34 is configured and chosen such that the sidewall 33 of the receptacle 32 experiences a radially outwardly directed stress as the insert section 22 is urged in the proximal direction into the receptacle 32. In this way the sidewall 33 of the receptacle 32 is somewhat splayed radially outwardly, allowing these abutment faces 24, 34 to travel past each other or to abut each other with relatively low force and stress when compared to a joint where the abutment faces were arranged perpendicular to the direction of assembly. In this way a sufficient travel is achieved to facilitate a mutual engagement of the fastening elements 25 and 35 configured as complementary-shaped snap features.

As shown in FIG. 5, the beveled axial end face 34 of the sidewall 33 of the receptacle 32 extends from a distal end of the sidewall 33 radially inwardly and in proximal direction 2. The beveled abutment face 24 of the flange section 23 is complementary-shaped. It extends from a distal and radially outwardly located end also radially inwardly in proximal direction 2.

Since the mutually corresponding fastening elements 25, 35 of cartridge holder 20 and body 30 are located at particular angular positions it is necessary to align and to correctly orientate the cartridge holder 20 and the body 30 with regard to their longitudinal axis before the insert section 22 is inserted into the receptacle 32. While the mutually corresponding fastening elements 25, 35 provide an axial interlock of cartridge holder 20 and body 30 there is provided at least one radial and axially extending rib 37 to engage with a complementary-shaped slot or groove 27.

Figure 1:
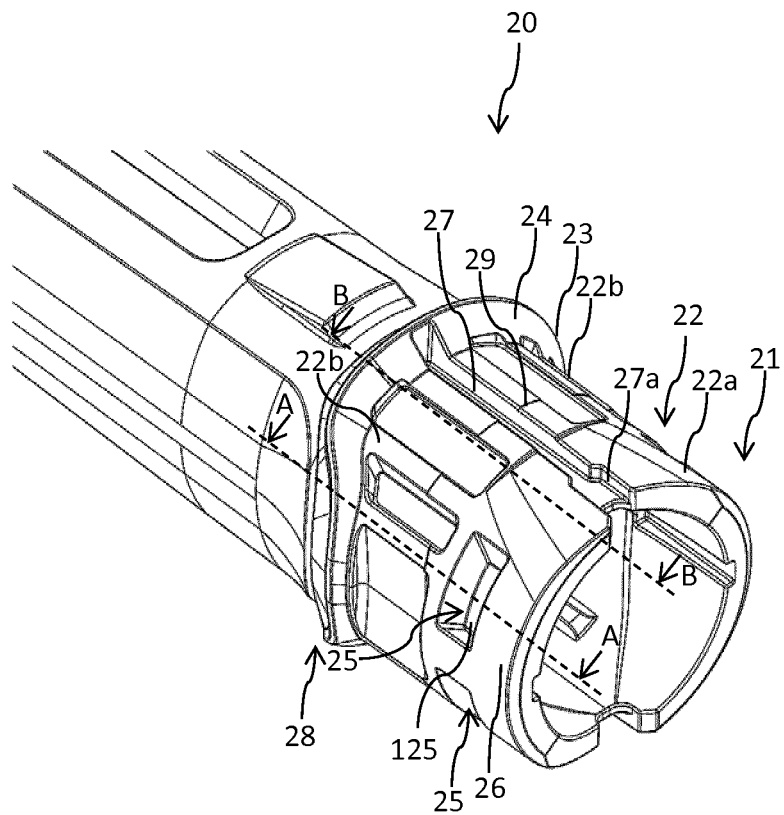
FIG. 1 shows a perspective view of a proximal end of a cartridge holder featuring an insert section.

In the illustrated embodiment the insert section 22 comprises at least one axially extending and radially recessed slot 27 extending from the proximal end of the insert section 22 to and into the flange section 23. On the inside of the sidewall 33 of the receptacle 32 there is provided a complementary-shaped radially extending rib 37 axially extending from the beveled and distal end face 34 towards and adjacent to the support 130. As it is illustrated in FIG. 1 the slot 27 comprises a circumferentially widened section 27*a* at its proximal end. Correspondingly, also the rib 37 comprises a circumferentially widened section 37*a* at its proximal end. The radially widened section 27*a* converges into a somewhat smaller rather straight-shaped main part of the slot 27 as seen in distal direction 1.

The circumferentially widened section 27*a* facilitates and supports proper and correct angular or rotational alignment of cartridge holder 20 and body 30 as the at least one rib 37 is inserted into the correspondingly-shaped slot 27. When the rib 37 engages the slot 27 the cartridge holder 20 is rotationally fixed to the body 30. In this way the mutual engagement of the slot 27 and the at least one rib 37 provides a rotational interlock of cartridge holder 20 and body 30. By means of the mutually engaging rib 37 and slot 27 the mutually corresponding fastening elements 25 and 35 of cartridge holder 20 and body 30 are correctly aligned so as to form the positive and irreleasable connection when the insert section 22 is fully or entirely inserted into the receptacle 32.

Figure 2:
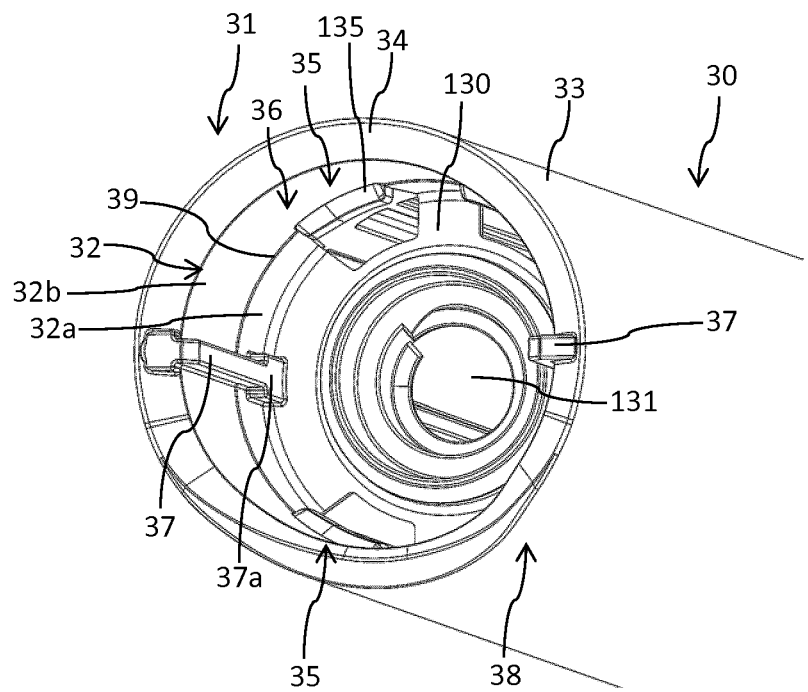
FIG. 2 shows a distal end of the body comprising a receptacle to receive an insert portion according to FIG. 1.
Figure 3:
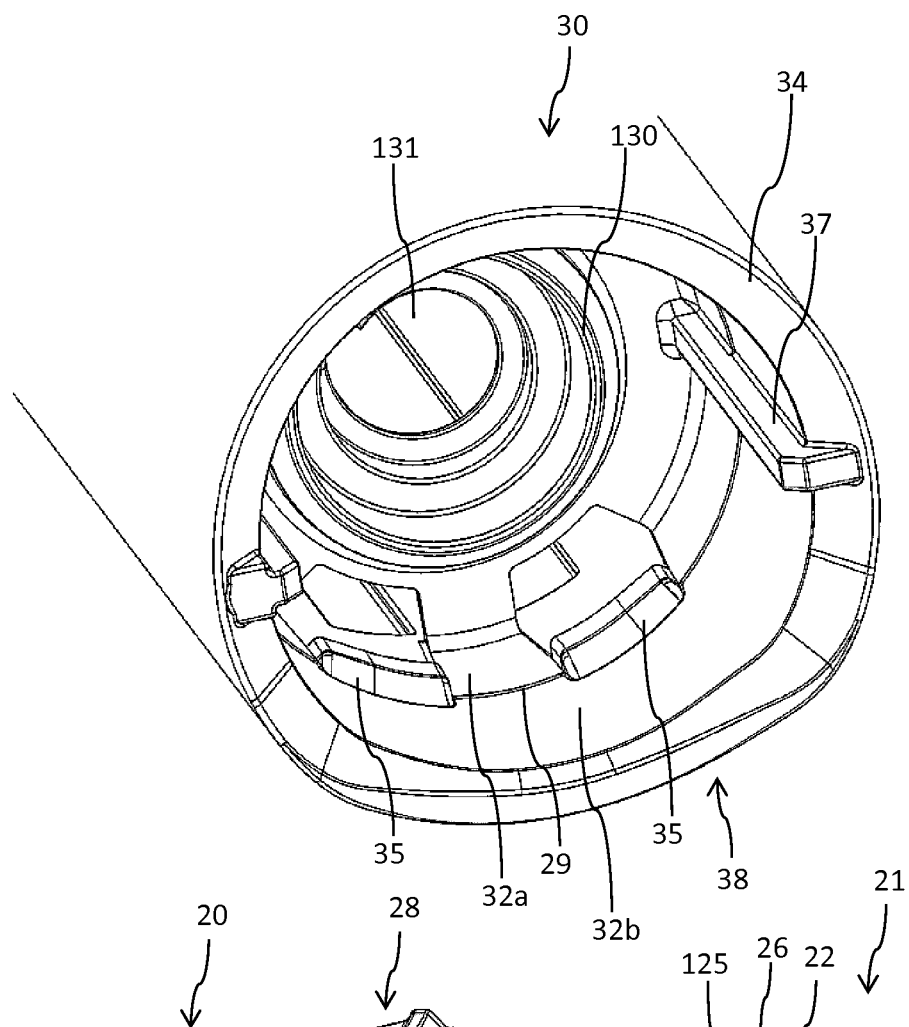
FIG. 3 is another perspective view of the distal end of the body according to FIG. 2.

The sidewall 33, in particular its distal end face 34 and the complementary-shaped flange section 23 on the outer surface of the cartridge holder 20 further comprise a symmetry breaking feature. As it is indicated in FIGS. 2, 4 and 5 the flange section 23 is of annular shape but does not completely extend in a transverse plane perpendicular to the longitudinal direction of the cartridge holder 20. As shown in FIG. 4, the flange section 23 comprises an axially protruded portion 28 that is located at a predefined proximal offset from the rest of the flange section 23. The sidewall 33 of the receptacle 32 comprises a complementary-shaped recessed portion 38, i.e. a proximally extending recess in the sidewall 33 adjacent to the distal end face 34 thereof. The recessed portion 38 and the protruded portion 28 are of complementary or corresponding shape. The protruded portion 28 matches and fits into the recessed portion 38. When there are two pairs of ribs 37 and mutually corresponding slots 27 as it is the case with the presently illustrated embodiment the cartridge holder 20 could be inserted into the receptacle 32 at two different angular orientations. With the symmetry breaking feature provided by the protruded portion 28 and the recessed portion 38 a unique angular orientation of cartridge holder and body is unequivocally defined.

It is of particular benefit when the at least one rib 37 and the at least one slot 27 are complementary-shaped free of clearance so that any play or backlash of cartridge holder 20 and body 30 can be reduced to a minimum.

Furthermore, it is intended that the insert section 22 comprises a free axial end section 22*a* as shown in FIG. 1 and an intermediate axial section 22*b* that is located axially between the free axial end section 22*a* and the flange section 23. Both the free axial end section 22*a* and the intermediate section 22*b* are of substantially tubular shape and are located axially adjacent. The interface between the free axial end section 22*a* and the intermediate section 22*b* is provided with a step 29 so that the outer diameter of the intermediate section 22*b* is slightly smaller than the outer diameter of the free axial end section 22*a*.

Correspondingly, also the inside of the sidewall 33 of the receptacle 32 comprises a free axial end section 32*b* adjacent to the beveled axial end face 34. Also there the free axial end section 32*b* is located axially adjacent to an intermediate section 32*a*. The intermediate section 32*a* is axially sandwiched between the support 130 and the free axial end section 32*b*. At least the free axial end section 22*a* of the insert section 22 and the intermediate section 32*a* of the receptacle 32 tightly match and are free of clearance so that the free axial end section 22*a* and the intermediate section 32*a* radially abut along the entire circumference thereof. In this way the interconnection allows to tolerance greater misalignment during assembly while maintaining a small draft angle which in turn is beneficial for a bending strength of the interconnection. In addition, it is also conceivable that not only the free axial end section 22*a* of the insert section 22 and the intermediate section 32*a* of the receptacle 32 tightly engage. Alternatively or additionally, it is also conceivable that the free axial end 32*b* of the receptacle 32 tightly engages with the intermediate section 22*b* of the insert section.

In the present embodiment it is the cartridge holder 20 that comprises the insert section 22 and it is the body 30 that comprises the receptacle 32. There are many different configurations conceivable, wherein for example it is the body 30 comprising a stepped down insert section to be assembled inside a proximally located receptacle of the cartridge holder. Also then it may be of particular benefit when it is the body that comprises the at least one axially extending slot to engage with a radially inwardly extending rib of the cartridge holder. Moreover, the mutually corresponding fastening elements to provide an axial interlock of cartridge holder 20 and body 30 could provide radial recesses in the distal end of the body and complementary-shaped protrusions on the proximal end of the cartridge holder.

As it is further shown in FIGS. 5 and 6 the cartridge holder 20 comprises numerous longitudinally or axially extending ribs 120 protruding radially inwardly from the inside of the tubular-shaped cartridge holder 20. Such ribs 120 may be regularly arranged along the entire circumference of the cartridge holder 20. The longitudinally extending ribs 120 effectively reduce the inner diameter of the cartridge holder 20. In this way the cartridge holder 20 is configured to receive correspondingly-shaped and rather small sized cartridges. It is particularly intended that the cartridge holder 20 is configured to accommodate small sized cartridges with a reduced inner volume and in particular with a reduced inner diameter compared to standard cartridges, that may provide a filling volume of about 3 ml. Small sized and volume-reduced cartridges to be inserted into the cartridge holder 20 may only comprise a filling volume of 1.5 ml. Generally, the diameter-reduced and hence volume-reduced or small sized cartridges may comprise an arbitrarily reduced volume compared to a standard cartridge. For instance, the filling volume of the small sized cartridge may be 1/r of the volume of a standard cartridge with r being a rational number larger than 1.

The cartridge holder 20 as illustrated in FIGS. 5 and 6 and hence the injection device 10 can be provided with a volume-reduced and diameter-reduced cartridge 50. This is of particular benefit to improve dosing accuracy and to deliver particularly small amounts or half dose increments of the medicament. Delivery of rather small doses with high precision is rather important in the field of pediatric treatment. With a standard sized cartridge delivery of small or even half or quarter doses is somewhat crucial as the advancing motion of the piston rod might be difficult to control when the travelling distance is fairly short.

By making use of a size and diameter-reduced cartridge a conventional and commercially available drive mechanism 5 can still be used. If for instance the inner cross-section of the cartridge is reduced by a factor 2 only half of the amount of the medicament will be delivered when the piston rod 110 advances in distal direction 1 over a predetermined distance that corresponds to a full dose size with a standard sized cartridge. By simply reducing the diameter of the cartridge 50 and by making use of a correspondingly configured cartridge holder 20 a conventional body with a conventional drive mechanism configured for operation with a standard sized cartridge can still be used. There, only a scale on a dose indicating member has to be replaced to indicate and to show the correct size of a dose.

In FIGS. 7 and 8 the injection device 10 is illustrated comprising a drive mechanism 5 that has been commercially distributed over years and which is described in detail in the following documents: WO 2004/078239 A1, WO 2004/078240 A2 and WO 2004/078241 A1. The injection device 10 is of disposable type. Hence, when the medicament 53 contained in the cartridge 50 has been dispensed or used up the entire device 10 is intended to be discarded. Therefore, the cartridge holder 20 to accommodate the cartridge 50 is irreleasably connectable to the proximal housing component, hence to the body 30. A cap 40 to cover the cartridge holder 20 extending distally from the body 30 is releasably interconnectable with the cartridge holder 20.

The drive mechanism 5 comprises numerous mechanically interacting components. The flange like support 130 of the body 30 comprises a threaded through opening 131 threadedly engaged with a distal thread 112 of the piston rod 110. The distal end of the piston rod 110 comprises a bearing 115 on which a pressure foot 116 is free to rotate with the longitudinal axis of the piston rod 110 as an axis of rotation. The pressure foot 116 is configured to axially abut against the proximally facing thrust receiving surface of the piston 52 of the cartridge 50. During a dispensing action the piston rod 110 rotates relative to the body 30 thereby experiencing a distally directed advancing motion relative to the body 30 and hence relative to the body 51 of the cartridge 50. As a consequence, the piston 52 of the cartridge 50 is displaced in distal direction by a well-defined distance due to the threaded engagement of the piston rod 110 with the body 30.

The piston rod 110 is further provided with a second thread 114 at its proximal end. The distal thread 112 and the proximal thread 114 are oppositely handed.

There is further provided a drive sleeve 100 having a hollow interior to receive the piston rod 110. The drive sleeve 100 comprises an inner thread threadedly engaged with the proximal thread 114 of the piston rod 110. Moreover, the drive sleeve 100 comprises an outer threaded section 105 at its distal end. The threaded section is axially confined between a distal flange section 102 and another flange section 104 located at a predefined axial distance from the distal flange section 102. Between the two flange sections 102, 104 there is provided a last dose limiting member 106 in form of a semi-circular nut having an internal thread matching the threaded section 105 of the drive sleeve 100.

The last dose limiting member 106 further comprises a radial recess or protrusion at its outer circumference to engage with a complementary-shaped recess or protrusion at an inside of the sidewall 33 of the body 30. In this way the last dose limiting member 106 is splined to the body 30. A rotation of the drive sleeve in a dose incrementing or clockwise direction during consecutive dose setting procedures leads to an accumulative axial displacement of the last dose limiting member 106 relative to the drive sleeve 100. There is further provided an annular spring 96 that is in axial abutment with a proximally facing surface of the flange section 104. Moreover, there is provided a tubular-shaped clutch member 90. At a first end the clutch member 90 is provided with a series of circumferentially directed saw teeth. Towards a second opposite end of the clutch member 90 there is located a radially inwardly directed flange.

Furthermore, there is provided a dose dial or dose indicating sleeve 80 and a spring 96. The clutch member 90 is located radially inward of the body 30. A helical groove 81 is provided about an outer surface of the dose indicating sleeve 80. The body 30 is provided with a window 44 through which a part of the outer surface of the dose indicating sleeve 80 can be seen. The body 30 is further provided with a helical rib at an inside sidewall portion of an insert piece 70, which helical rib is to be seated in the helical groove 81 of the dose indicating sleeve 80. The tubular shaped insert piece 70 is inserted into the proximal end of the body 30. It is rotationally and axially fixed to the body 30. There are provided first and second stops on the body 30 to limit a dose setting procedure during which the dose indicating sleeve 80 is rotated in a helical motion relative to the body 30.

A dose dial grip 66 is disposed about an outer surface of the proximal end of the dose indicating sleeve 80. An outer diameter of the dose dial 66 typically corresponds to the outer diameter of the body 30. The dose dial 66 is secured to the dose indicating sleeve 80 to prevent relative movement therebetween. The dose dial 66 is provided with a central opening.

Furthermore, a dose button 60 of generally T-shape is provided at a proximal end of the injection device 10. A stem 62 of the dose button 60 extends through the opening in the dose dial 66 through an inner diameter of extensions of the drive sleeve 100 and into a receiving recess at the proximal end of the piston rod 110. The stem 62 is retained for limited axial movement in the drive sleeve 100 and against rotation with respect thereto. A head 64 of the dose button 60 is generally circular. A skirt extends from a periphery of the head 64 and is further adapted to be seated in a proximally accessible annular recess of the dose dial 66.

To dial a dose a user rotates the dose dial 66. With the spring 96 also acting as a clicker and the clutch member 90 engaged, the drive sleeve 100 the spring or clicker 96, the clutch member 90 and the dose indicating sleeve 80 rotate with the dose dial 66. Audible and tactile feedback of the dose being dialed is provided by the spring 96 and by the clutch member 90. Torque is transmitted through saw teeth between the spring 96 and the clutch member 90. The helical groove 81 on the dose indicating sleeve 80 and a helical groove in the drive sleeve 100 have the same lead. This allows the dose indicating sleeve 80 to extend from the body 30 and the drive sleeve 100 to climb the piston rod 110 at the same rate. At a limit of travel a radial stop on the dose indicating sleeve 80 engages either with a first stop or a second stop provided on the body 30 to prevent further movement. Rotation of the piston rod 110 is prevented due to the opposing directions of the overall and driven threads on the piston rod 110.

The last dose limiting member 106 keyed to the body is advanced along the threaded section 105 by the rotation of the drive sleeve 100. When a final dose dispensed position is reached, a radial stop formed on a surface of the last dose limiting member 106 abuts a radial stop on the flange section 104 of the drive sleeve 100, preventing both, the last dose limiting member 106 and the drive sleeve 100 from rotating further.

Should a user inadvertently dial beyond the desired dosage, the pen-injector 10 allows the dosage to be dialed down without dispense of the medicament from the cartridge 50. For this the dose dial 66 is simply counter-rotated. This causes the system to act in reverse. A flexible arm of the spring or clicker 96 then acts as a ratchet preventing the spring 96 from rotating. The torque transmitted through the clutch member 90 causes the saw teeth to ride over one another to create the clicks corresponding to dialed dose reduction. Typically, the saw teeth are so disposed that a circumferential extent of each saw tooth corresponds to a unit dose.

When the desired dose has been dialed the user may simply dispense the set dose by depressing the dose button 60. This displaces the clutch member 90 axially with respect to the dose indicating sleeve 80 causing dog teeth thereof to disengage. However, the clutch member 90 remains keyed in rotation to the drive sleeve 100. The dose indicating sleeve 80 and the dose dial 66 are now free to rotate in accordance with the helical groove 81.

The axial movement deforms the flexible arm of the spring 96 to ensure the saw teeth cannot be overhauled during dispense. This prevents the drive sleeve 100 from rotating with respect to the body 30 though it is still free to move axially with respect thereto. The deformation is subsequently used to urge the spring 96 and the clutch member 90 back along the drive sleeve 100 to restore the connection between the clutch member 90 and the dose indicating sleeve 80 when the distally directed dispensing pressure is removed from the dose button 60.

The longitudinal axial movement of the drive sleeve 100 causes the piston rod 110 to rotate through the through opening 131 of the support 130 of the body, thereby to advance the piston 52 in the cartridge 50. Once the dialed dose has been dispensed, the dose indicating sleeve 80 is prevented from further rotation by contact of a plurality of members extending from the dose dial 66 with a corresponding plurality of stops. A zero dose position is finally determined by the abutment of one of axially extending edges of members of the dose indicating sleeve 80 with a corresponding stop of the body 30.

The drive mechanism 5 as described above is only exemplary for one of a plurality of differently configured drive mechanisms that are generally implementable in a disposable pen-injector.

Hence, the interface and interconnection of housing components, such like the cartridge holder 20 and the body 30 as explained above can be generally implemented with a large variety of different drive mechanisms.

LIST OF REFERENCE NUMBERS 1 distal direction
2 proximal direction
5 drive mechanism
6 axial interlock
10 injection device
11 housing
19 threaded socket
20 cartridge holder
21 proximal connecting end
22 insert section
22a end section
22b intermediate section
23 flange section
24 abutment face
25 fastening element
26 outside wall
27 slot
27a widened section
28 protruded portion
29 step
30 body
31 distal connecting end
32 receptacle
32a intermediate section
32b end section
33 sidewall
34 end face
35 fastening element
36 inside wall
37 rib
37a widened section
38 recessed portion
39 step
40 cap
44 window
50 cartridge
51 barrel
52 piston
53 medicament
54 seal
60 dose button
62 stem
64 head
66 dose dial
70 insert
80 dose indicating sleeve
81 helical groove
90 clutch member
96 spring
100 drive sleeve
102 distal flange section
104 flange section
105 threaded section
106 last dose limiting member
110 piston rod
112 distal thread
114 proximal thread
115 bearing
116 pressure foot
125 recess 125a beveled section
126 abutment section
127 beveled edge
130 support
131 through opening
135 protrusion
135a beveled section
136 abutment section

The invention claimed is:

1. An elongated housing for an injection device for delivery of a liquid medicament, the elongated housing comprising:
   a tubular-shaped cartridge holder to accommodate a cartridge filled with the liquid medicament and comprising a proximal connecting end; and
   a body to accommodate a drive mechanism operably engageable with a piston of the cartridge, wherein the body comprises a distal connecting end connectable to the proximal connecting end of the tubular-shaped cartridge holder,
   wherein one of the proximal connecting end of the tubular-shaped cartridge holder and the distal connecting end of the body comprises an insert section,
   wherein the other one of the proximal connecting end of the tubular-shaped cartridge holder and the distal connecting end of the body comprises a receptacle to axially receive the insert section,
   wherein the insert section comprises a fastening element to positively engage with a complementary-shaped fastening element of the receptacle to provide an axial interlock between the tubular-shaped cartridge holder and the body, and wherein the insert section is axially confined by a radially outwardly extending flange section, the flange section comprising an annular shaped non-planar flange portion,
   wherein the fastening element of the insert section and the complementary-shaped fastening element of the receptacle comprise a radial protrusion mating with a radial recess, one of the radial protrusion and the radial recess being on an inside wall of the receptacle, and the other of the radial protrusion and the radial recess being on an outside wall of the insert section,
   wherein a radial depth of the radial recess is smaller than a thickness of a sidewall of the insert section or a thickness of a sidewall of the receptacle,
   wherein the sidewall of the receptacle comprises an annular shaped non-planar axial end face, and
   wherein the annular shaped non-planar axial end face is complementary shaped to the annular shaped non-planar flange portion and is configured to mate with the annular shaped non-planar flange portion.

2. The elongated housing according to claim 1, wherein:
   the insert section comprises a free axial end portion and an intermediate portion located axially between the free axial end portion of the insert section and the flange section,
   a diameter of the free axial end portion of the insert section is smaller than the diameter of the intermediate portion of the insert section, and
   the receptacle comprises a free axial end portion and an axially adjacent intermediate portion, at least the intermediate portion of the receptacle being complementary-shaped to the free axial end portion of the insert section.

3. The elongated housing according to claim 1, wherein the annular shaped non-planar axial end face is a beveled axial end face complementary-shaped to a beveled abutment face of the flange section.

4. The elongated housing according to claim 3, wherein the beveled axial end face of the receptacle and the beveled abutment face are configured to face in opposite axial directions and to be in mutual abutment when the insert section reaches a fastening position inside the receptacle.

5. The elongated housing according to claim 3, wherein an axial distance between the complementary-shaped fastening element of the receptacle and the beveled axial end face is larger than or equal to an axial distance between the fastening element of the insert section and the beveled abutment face of the flange section.

6. The elongated housing according to claim 3, wherein the beveled axial end face and the beveled abutment face are shaped to generate a radially inwardly directed load on the insert section when the beveled axial end face and the beveled abutment face are subject to an axial compression.

7. The elongated housing according to claim 3, wherein the beveled axial end face and the beveled abutment face are shaped to generate a radially outwardly directed load on the receptacle when the beveled axial end face and the beveled abutment face are subject to an axial compression.

8. The elongated housing according to claim 1, wherein:
   one of the insert section and the receptacle comprises an axially extending radial slot, and
   the other one of the insert section and the receptacle comprises a radial protrusion or an axially extending radial rib complementary-shaped to the axially extending radial slot.

9. The elongated housing according to claim 8, wherein the axially extending radial slot and the axially extending radial rib are axially insertable into each other free of clearance.

10. The elongated housing according to claim 8, wherein the radial slot and the radial protrusion or radial rib form a rotational interlock of receptacle and insert section configured to engage prior to or during insertion of the insert section into the receptacle, wherein the radial slot and the radial protrusion or radial rib engage prior to a mutual engagement of the fastening element of the insert section with the complementary-shaped fastening element of the receptacle.

11. The elongated housing according to claim 8, wherein the radial slot adjoins an axial edge of at least one of the outside wall of the insert section and the inside wall of the receptacle.

12. The elongated housing according to claim 8, wherein the radial protrusion or radial rib adjoins an axial edge of at least one of the inside wall of the receptacle and the outside wall of the insert section.

13. The elongated housing according to claim 1, wherein:
   the insert section forms the proximal connecting end of the tubular-shaped cartridge holder, and
   the receptacle forms the distal connecting end of the body.

14. The elongated housing according to claim 1, wherein:
   the fastening element of the receptacle comprises the radial protrusion, and
   the fastening element of the insert section comprises the radial recess.

15. The elongated housing according to claim 1, wherein the insert section comprises a plurality of fastening elements to positively engage with a plurality of complementary-shaped fastening elements of the receptacle to provide the axial interlock between the tubular-shaped cartridge holder and the body.

16. The elongated housing according to claim 1, wherein an axial position of the annular shaped non-planar axial end face varies along a circumference of the annular shaped non-planar axial end face and an axial position of the annular shaped non-planar flange portion varies along a circumference of the annular shaped non-planar flange portion.

17. The elongated housing according to claim 1 wherein the annular shaped non-planar axial end face comprises one of an axially protruding portion and an axially recessed portion extending axially from the annular shaped non-planar axial end face to mate with one of a complementary-shaped axially recessed portion and an axially protruding portion extending axially from the annular shaped non-planar flange portion of the flange section.

18. An injection device for delivery of a liquid medicament comprising:
    a housing comprising
        a tubular-shaped cartridge holder to accommodate a cartridge filled with the liquid medicament and comprising a proximal connecting end; and
        a body to accommodate a drive mechanism operably engageable with a piston of the cartridge, wherein the body comprises a distal connecting end connectable to the proximal connecting end of the tubular-shaped cartridge holder,
    wherein one of the proximal connecting end of the tubular-shaped cartridge holder and the distal connecting end of the body comprises an insert section,
    wherein the other one of the proximal connecting end of the tubular-shaped cartridge holder and the distal connecting end of the body comprises a receptacle to axially receive the insert section,
    wherein the insert section comprises a fastening element to positively engage with a complementary-shaped fastening element of the receptacle to provide an axial interlock between the tubular-shaped cartridge holder and the body, and wherein the insert section is axially confined by a radially outwardly extending flange section, the flange section comprising an annular shaped non-planar flange portion,
    wherein the fastening element of the insert section and the complementary-shaped fastening element of the receptacle comprise a radial protrusion mating with a radial recess, one of the radial protrusion and the radial recess being on an inside wall of the receptacle, and the other of the radial protrusion and the radial recess being on an outside wall of the insert section, and
    wherein a radial depth of the radial recess is smaller than a thickness of a sidewall of the insert section or a thickness of a sidewall of the receptacle,
    wherein the sidewall of the receptacle comprises an annular shaped non-planar axial end face,
    wherein the annular shaped non-planar axial end face is complementary shaped to the annular shaped non-planar flange portion and is configured to mate with the annular shaped non-planar flange portion; and
    a drive mechanism arranged inside and fixed to the body of the housing.

19. The injection device according to claim 18, further comprising the cartridge,
    wherein the cartridge is filled with a liquid medicament and is arranged inside the tubular-shaped cartridge holder, and
    wherein the tubular-shaped cartridge holder is irreleasably connected to the body.

20. The injection device according to claim 18, wherein the annular shaped non-planar axial end face is a beveled axial end face complementary-shaped to a beveled abutment face of the flange section.

21. The injection device according to claim 20, wherein the beveled axial end face of the receptacle and the beveled abutment face are configured to face in opposite axial directions and to be in mutual abutment when the insert section reaches a fastening position inside the receptacle.

22. The injection device according to claim 18, wherein an axial position of the annular shaped non-planar axial end face varies along a circumference of the annular shaped non-planar axial end face and an axial position of the annular shaped non-planar flange portion varies along a circumference of the annular shaped non-planar flange portion.

23. The injection device according to claim 18, wherein the annular shaped non-planar axial end face comprises one of an axially protruding portion and an axially recessed portion extending axially from the annular shaped non-planar axial end face to mate with one of a complementary-shaped axially recessed portion and an axially protruding portion extending axially from the annular shaped non-planar flange portion of the flange section.

* * * * *

UNITED STATES PATENT AND TRADEMARK OFFICE
CERTIFICATE OF CORRECTION

| | | |
|---|---|---|
| PATENT NO. | : 11,400,218 B2 | Page 1 of 1 |
| APPLICATION NO. | : 15/559300 | |
| DATED | : August 2, 2022 | |
| INVENTOR(S) | : Robert Veasey, David Aubrey Plumptre and Matthew Jones | |

It is certified that error appears in the above-identified patent and that said Letters Patent is hereby corrected as shown below:

In the Claims

Column 24, Line 60, Claim 14, delete "w herein:" and insert -- wherein: --

Signed and Sealed this
Twentieth Day of September, 2022

*Katherine Kelly Vidal*

Katherine Kelly Vidal
*Director of the United States Patent and Trademark Office*